United States Patent [19]

Herz et al.

[11] E Re. 28,668

[45] Reissued Dec. 30, 1975

[54] SILVER HALIDE EMULSIONS CONTAINING ALKYL SELENOLS AND THIOLS AS ANTIFOGGANTS

[75] Inventors: Arthur H. Herz, Rochester, N.Y.; Edwin R. Westcott, New Smyrna Beach, Fla.

[73] Assignee: Eastman Kodak Company, Rochester, N.Y.

[22] Filed: Apr. 3, 1975

[21] Appl. No.: 564,960

Related U.S. Patent Documents

Reissue of:

[64] Patent No.: 3,732,103
Issued: May 8, 1973
Appl. No.: 139,941
Filed: May 3, 1971

[52] U.S. Cl. ..... 96/76 R; 96/77; 96/68; 96/95; 96/100; 96/109

[51] Int. Cl.² ..... G03C 1/34; G03C 1/48

[58] Field of Search ..... 96/76 R, 77, 95, 100, 109, 96/68

[56] References Cited

UNITED STATES PATENTS

| | | | |
|---|---|---|---|
| 2,131,038 | 9/1938 | Brooker | 96/109 |
| 3,042,521 | 7/1962 | Dersch, et al. | 96/109 |
| 3,506,444 | 4/1970 | Haist et al. | 96/109 |
| 3,535,115 | 10/1970 | Weber | 96/109 |
| 3,615,621 | 10/1971 | Lamon | 96/109 |

*Primary Examiner*—Won H. Louie, Jr.
*Attorney, Agent, or Firm*—C. O. Thomas

[57] ABSTRACT

Photographic silver halide emulsions and elements comprising said emulsions are stabilized against fog by organic selenium derivatives and their sulfur-containing analogs. New alkyl selenols useful in fog stabilizing concentrations are likewise disclosed.

These fog stabilizing organic compounds have the structural formula:

(I)

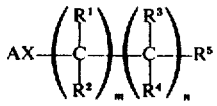

in which A is a cation, X is sulfur or selenium, $R^1$ to $R^5$ are each hydrogen or organic residues provided that at least one of said $R^1$ to $R^5$ is a sulfonic acid group or salt thereof and m and n are each about 0 to about 4 so that the sum of m and n equals a positive integer up to about 8;

(II)

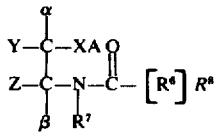

or

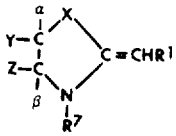

in which A is a cation, X is sulfur or selenium, $R^7$ is an organic residue; $R^6$ is hydrogen or an organic residue; $R^8$ *is an organic residue;* $\alpha$ and $\beta$ are each hydrogen, organic residue or the electrons required to form double bonds between the carbon atoms; Y and Z are each hydrogen or an organic residue or together comprise atoms needed to complete a cyclic nucleus.

12 Claims, No Drawings

SILVER HALIDE EMULSIONS CONTAINING ALKYL SELENOLS AND THIOLS AS ANTIFOGGANTS

Matter enclosed in heavy brackets [ ] appears in the original patent but forms no part of this reissue specification; matter printed in italics indicates the additions made by reissue.

*CROSS-REFERENCE TO RELATED APPLICATION*

*This application is a reissue of U.S. Patent 3,732,103, based on U.S. Serial No. 139,941, filed May 3, 1971.*

BACKGROUND OF THE INVENTION

Field of the invention

This invention relates to the stabilization of photographic elements and compositions. More particularly it relates in one aspect to the stabilization of silver halide containing compositions against spontaneous fog. In another aspect, the invention relates to certain new and known organic selenium derivatives and their sulfur-containing analogs which are useful in stabilizing light sensitive silver halide emulsions and layers of photographic elements.

DESCRIPTION OF THE PRIOR ART

It is well known in the art that photosensitive silver halide emulsions and layers tend to lose their sensitivity and spontaneously develop without exposure to light. The detectable amount of silver salt reduced during development of those unexposed areas is commonly referred to as "fog" and more specifically, chemical fog.

While the degree of fog depends in part on the particular emulsion and conditions of development, fog usually increases with increases in time, temperature and relative humidity of storage conditions.

Various addenda have been employed in the past to increase the stability of the photosensitive silver halide-containing elements and compositions. Some such addenda reduce the tendency to fog but likewise exhibit the disadvantage of decreasing the sensitivity and/or the contrast of the silver halide-containing element and composition. This is especially true in those photographic preparations which are optically sensitized to the various spectral regions, such as those preparations adapted for use in color photography.

While it is known that organic sulfur and selenium derivatives might exhibit similar antifoggant and stabilizing properties; such selenium compounds do not appear to differ from their corresponding sulfur compounds.

For example, while in U.S. Patent 2,195,150 issued Mar. 26, 1940, to Kendall, there are described various selenamercapto-4-hydroxy pyrimidines as fog-stabilizers, the use of both mercapto-containing compounds and pyrimidines has been reported thereafter, such as in U.S. Pat. 2,819,965 and 2,935,404 issued Jan. 14, 1958 and May 3, 1960 respectively.

However, because of the peculiar nature of the antifogging and stabilizing compounds and their effect on the silver halide-containing element, it is not believed that even those persons skilled in the art can predict the effectiveness of various compounds with any certainty or justification. Consequently, it is not surprising to learn from various references such as U.S. Patent 3,284,206 issued Nov. 8, 1966, to Blake that certain silver salts of organic selenols are useful in greater than fog-inhibiting amounts as photo-solubilizers due to their lower solubility in water than silver chloride.

British Pat. 1,115,048 issued May 22, 1968, to McVeigh discloses the use of organic selenium compounds as sensitizers for silver halide emulsions. Similarly in British 1,098,466 issued to Dunn, Jan. 10, 1968, small amounts of organic selenium derivatives are used in conjunction with noble metal sensitizers in order to produce unexpected increases in sensitivity.

In Polaroid British Pat. 1,080,228 issued Aug. 23, 1967, the prior art discussion refers to U.S. Pat. 2,131,038 of Brooker issued Sept. 27, 1938, wherein N-alkyl substituted azoles containing an oxygen, sulfur or selenium atom as a component of the azole ring are disclosed as photographic antifogging agents which, however, appear to desensitize the emulsions in which they are placed. The modification of the prior art compounds of U.S. Pat. 2,131,038 to their N-carboxyalkyl or N-sulfoalkyl analogs provided the unexpected properties of good emulsion stabilization against fog without desensitization. This reference further emphasizes the unpredictability of acceptable emulsion stabilization and antifogging properties of seemingly related compounds and particularly those containing the sulfur or selenium atom.

Since many prior art antifoggants and emulsion stabilizers also provide unwanted desensitizing activity, the need still exists for such addenda which exhibit substantially only fog restraining properties.

SUMMARY OF THE INVENTION

This invention relates to new photographic compositions and elements comprising light sensitive silver halide which is fog stabilized by an effective concentration of a selenium- or sulfur-containing organic compound. These compounds are generically described as sulfoalkyl selenols and their thiol analogs, β-acylamino alkylene selenols and their thiol analogs and methylene bases such as 2-methyleneselenazolines and their thiazoline analogs.

It is an object of this invention to provide photographic silver halide-containing compositions and elements which are stabilized against fog. It is another object of this invention to stabilize emulsions and layers of silver halide without adversely affecting to any substantial degree, the photographic sensitivity of said silver halide.

It is still another object of the present invention to provide new compounds which are useful in accomplishing these and other objects.

A further object of the invention is to provide stabilized silver halide containing compositions and elements comprising development modifiers by employing certain selenium-containing organic compounds and their sulfur anologs such as thiols or thiazolines.

Still other objects will become apparent from an examination and reading of the specification and claims which follow.

DESCRIPTION OF PREFERRED EMBODIMENTS

In accordance with our invention, it has been found that certain selenium-containing organic compounds and their sulfur analogs act as effective fog-stabilizers and antifoggants for silver halide emulsions and layers without causing significant reduction in their photographic sensitivity. These compounds have the general formula:

(I)

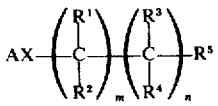

where A represents an organic or inorganic cation, X is either sulfur or selenium and $R^1$ to $R^5$ are each hydrogen or organic residues such as a hydrocarbon residue or functionally substituted hydrocarbon group provided that at least one of said $R^1$ to $R^5$ groups is a sulfonic acid group ($-SO_3H$) or an organic or inorganic salt thereof, like sodium, potassium, guanidinium and the like; and m is about 0 to about 4 and n is about 0 to about 4; so that the sum of m and n is a positive integer of up to about 8.

(II)

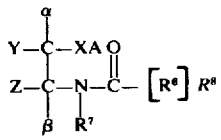

in which A is an organic or inorganic cation, X is either sulfur or selenium and $R^7$ is an organic residue such as hydrocarbon groups exemplified by alkyl residues like those having 1 to 6 carbon atoms like methyl; aryl residues like benzyl and the like or functionally-substituted alkyl residues such as sulfopropyl and the like in addition to carboxyalkyl like carboxydecyl and hydroxyalkyl like hydroxyethyl and the like; [$R^6$ is hydrogen or an organic residue such as a hydrocarbon group like $R^7$,] *$R^8$ is an organic residue such as a hydrocarbon group like $R^7$*, and $\alpha$ and $\beta$ are hydrogen or an organic residue such as hydrocarbon groups like $R^7$ or can represent the electrons needed to link the carbon atoms to which they are attached by a double bond; Y and Z are hydrogen or a hydrocarbon residue like $R^7$ or together provide the linkage required for completion of a mono-cyclic nucleus like pyridine or benzene or polycyclic nuclei where a 5–6 membered ring is further fused to the mono-cyclic nucleus such as the structure of

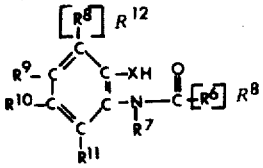

in which X, [$R^6$] $R^8$ and $R^7$ have the same values as in Formula II and [$R^8$,] $R^9$, $R^{10}$ [and] $R^{11}$ *and $R^{12}$* can each be hydrogen, halogen, a nitro group or a condensed polycyclic nucleus such as naphthalene and the like or (III)

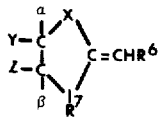

which monomer may interconvert to the dimer

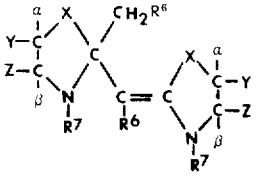

in which [$R^6$] $R^8$, $R^7$, $\alpha$, $\beta$, Y, Z and X have the same values as in (II). *$R^6$ is hydrogen or an organic residue such as a hydrocarbon group like $R^7$*. The dimer is included herein where the monomer is specified since it is believed well known from Tetrahedron Letters 32, 2709 (1969) that the monomeric and dimeric methylene bases are readily interconverted as shown.

It will be understood that use of the term organic cation can be exemplified by ions such as guanidinium, tetraalkylammonium, trialkylsulfonium and the like and inorganic cations include those such as hydrogen, sodium, potassium and related ions. Organic residues can be hydrocarbon residues like the alkyl groups such as lower alkyl like those having 1 to 6 carbons including methyl, ethyl, butyl, isopropyl and the like and functionally substituted hydrocarbon groups exemplified by substituted alkyls such as haloalkyl, hydroxyalkyl and various aryl substituted alkyls. These include hydroxyethyl, chloroethyl, phenylethyl, chloronaphthyl, substituted pyridiyl and the like. Mono-cyclic or polycyclic nuclei are well known and include phenyl, naphthyl, pyridyl and the like groups.

Among the various compounds which are included in the structure of Formula I are: guanidinium-2-selenylpropane sulfonate; guanidinium-3-selenyl-3-methylpropanesulfonate; guanidinium-2-mercaptoethane sulfonate; guanidinium-4-mercaptobutane, sulfonate and the like.

Typical of compounds which are defined by the Formula II include for example:

2(N-ethylacetamido)propane-1-thiol;
2(N-ethylacetamido)propane-1-selenol;
2(N-methylpropionamido)propene-1-thiol;
2(N-methylpropionamido)propene-1-selenol;
[2(N-sulfobutylformamido)ethene-1-selenol;]
2(N-methylacetamidol)ethene-1-thiol;
2(N-dodecylacetamido)-ethane-1-thiol;
o-(N-ethylacetamido)thiophenol;
o-(N-methylacetamido)-6-nitroselenaphenol;
o-(N-sulfobutylacetamido)thiophenol;
o-(N-sulfobutylacetamido)selenophenol;
2(N-sulfobutylformamido)ethane-1-selenol;
2(N-carboxymethylacetamido)propane-1-thiol;
[o-(N-ethoxycarbonylformamido)thiophenol;]
o-(N-phenylformamido)thiophenol;
o-(N-ethylacetamido)-5-chlorothiophenol;
o-(N-ethylacetamido)selenaphthol
and the like.

Likewise representative examples of compounds included within the definition of structural Formula III include: 3-methyl-2-methylene benzoselanazoline and its sulfur analog, 3-methyl-2-methylene benzothiazoline and the like.

The stabilizing compounds defined by these structural formulae can be utilized in a variety of ways such as being incorporated directly into silver halide containing elements, such as in the silver halide layer, silver halide emulsions or in various layers contiguous thereto such as overcoat, intermediate and the like layers. In this manner it can be said that these selenium containing antifoggant compounds or their sulfur analogs are incorporated into photographic elements and compositions in a concentration and manner sufficient to insurea fog-inhibiting effect. This relationship is likewise insured by use of said compounds in various solutions or sprays in which the finished or processed photographic material is so stabilized or in using various wrapping or storage materials or environments juxtaposed to the layers, emulsion or elements.

In another preferred embodiment the compounds within the scope defined by the above formulae are effective antifoggants and emulsion stabilizers when employed either in or contiguous to a photographic silver halide gelatin-containing emulsion layer. A preferred concentration of said compounds is from about 0.005 to about 1.0 gram per mole of silver halide.

Still another preferred embodiment resides in photographic silver halide emulsions which further comprise color-coupler forming compounds such as those which are phenolic, pyrazolone and open-chain reactive methylene compounds which are capable of forming a dye with the oxidation product of an aromatic primary amine silver halide color developing agent. In yet another embodiment of the invention there is provided a photographic element comprising a support bearing a fog stabilized light sensitive silver halide-containing layer and comprising a silver halide solvent concentration of a selenium-containing organic compound or its sulfur analog having the structural formula:

(I)

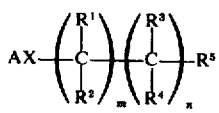

in which A is a cation, X is sulfur or selenium, $R^1$ to $R^5$ are hydrogen or organic residues such as a hydrocarbon residue or functionally substituted hydrocarbon groups provided that at least one of said $R^1$ to $R^5$ groups is a sulfonic acid group ($-SO_3H$) or an organic or inorganic salt thereof, like sodium, potassium, guanidinium and the like; and m is about 0 to about 4 and n is from about 0 to 4 or (II)

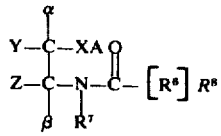

or (III)

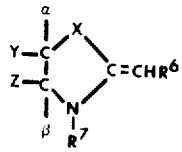

in which A is a cation, X is sulfur or selenium, $R^7$ is an organic residue; *$R^8$ is an organic residue;* $R^6$ is hydrogen or an organic residue; $\alpha$ and $\beta$ are each hydrogen, an organic residue or the electrons required to form double bonds between the carbon atoms; Y and Z are each hydrogen or an organic residue or together comprise atoms needed to complete a cyclic nucleus.

The sulfoalkyl thiols and selenols described in Formula I are conveniently prepared by well known methods such as the Schramm procedure described in U.S. Pat. 2,695,310 and in JACS 77, 6321 (1955). These compounds are effective as antifoggants in a concentration range of from about 0.005 to about 1.0 gram/mole silver halide and preferably from about .01 to about 0.5. At higher concentrations, these compounds are unexpectedly effective as silver halide solvents. As will be seen hereafter, these compounds will stabilize the sensitivity of the emulsions and restrain the formation of development and incubation fog. In the examples following, these compounds can also restrain the fog associated with the presence of cationic (for example pyridinium) development accelerators.

The $\beta$-acylamino thiols and selenols likewise have an effective antifoggant concentration in the range from about 0.005 to about 1.0 gram/mole of silver halide. We have unexpectedly found that compounds having the structural formula of (II) having between about 4 and about 8 carbon atoms, can be used at elevated concentrations, i.e. about 1 to about 50 grams/mole of silver as silver halide solvents. When these compounds contain more than about 8 carbon atoms and also include a solubilizing group such as a carboxylic acid or a sulfonic acid substituent, they also are effective as a silver halide solvent.

These compounds having structural Formula II can be obtained by a variety of methods such as by reduction of the corresponding disulfide or diselenide [ or by the hydrolysis of the corresponding quaternary azolium salt or their related methylene bases ], which methods of preparation are disclosed in Larive et al., Chimia 15, 115, 1961 and in J. Chim. Phys. 60, 944, 1963 and by Mills and Clark in J. Chem. Soc. 2353 (1923); 2805 (1927) and 2313 (1928).

Likewise we have found that it is unnecessary to isolate the thiols or selenols and they can be conveniently prepared by treating the dissolved azolium salt with two equivalents of suitable base in water or a methanol-water mixture which is then added to the emulsion. As is well known in the art, potentiometry can be used to ascertain the formation of the resulting thiol or selenol.

Preferred concentration ranges effective for antifoggant purposes similar to those above disclosed exist for the methylene bases described in Formula III, i.e. for fog-restraining purposes effective ranges are 0.005 to about 1.0 gram/mole silver halide. These antifoggants are conveniently prepared by methods disclosed in Belgian Pat. 744,886 issued Jan. 24, 1969, to Owen and can be likewise prepared as disclosed in J. Pr. Chem. 109, 324 (1925) by Konig and Meier.

The sulfoalkyl selenols and thiols having the structural Formula I can likewise serve as silver halide solvent ripening agents in the preparation of silver halide emulsions, as fixing agents, or as silver solvents in diffusion transfer processes. Because of their crystallizability the guanidinium sulfonates of these compounds have unexpectedly provided significantly good results. They are prepared conveniently by the Schramm method (supra) and include guanidinium - 3 - selenyl - 3 -methyl propane sulfonate, guanidinium - 2 - selenylpropane sulfonate, guanidinium mercaptobutane sulfonate and the like.

When the subject addenda are used as fixing agents for photographic silver halide emulsions, about one mole of additive is utilized for each mole of silver halide in the emulsion. In addition, these sulfur or selenium-containing addenda can be used with significant unexpected advantage to achieve enhanced ripening or digestion of the emulsion. As such, they can be added before the final digestion or the after-ripening.

For this procedure, the subject class of sulfur and selenium compounds are effective in concentrations of from about 1 to about 50 grams/mole of silver. The various operations of emulsion making can be described briefly as in Mees, The Theory of the Photographic Process, 1954 as (1) emulsification and digestion of the silver halide; (2) freeing of the emulsion of excess water-soluble salts, suitably by washing, with water; and (3) the second digestion or "after-ripening" in order to achieve increased emulsion speed or sensitivity. Particularly useful addenda are those set forth above in Formula II wherein at least one R is an acid residue such as carboxylic, sulfinic, sulfonic acid substituents and the like. In the latter instances, silver halide solvent properties exist when the compounds contain more than 8 carbon atoms. In the alternative, as those compounds of Formula I provide when only 4 to 8 carbon atoms exist, no solubilizing group need appear and elevated temperatures, i.e. greater than ambient, are employed for preferred solvent action.

The silver halide emulsions used in the practice of this invention can be additionally protected against the production of fog and can be stabilized against loss of sensitivity during keeping. Suitable other antifoggants and stabilizers each used alone or in combination include the azaindenes described in Piper U.S. Pat. 2,886,437 issued May 12, 1959 and Heimbach et al. U.S. Pat. 2,444,605 issued July 6, 1948; the mercury salts as descrbied in Allen et al. U.S. Pat. 2,728,663 issued Dec. 27, 1955; the urazoles described in Anderson et al. U.S. Pat. 3,287,135 issued Nov. 22, 1966; the sulfocatechols described in Kennard et al. U.S. Pat. 3,236,652 issued Feb. 20, 1966; the oximes described in Carroll et al. British Pat. 623,448; nitron; nitroindazoles; the mercaptotetrazoles described in Kendall et al. U.S. Pat. 2,403,927 issued July 16, 1946; Kennard et al. U.S. Pat. 3,266,897 issued Aug. 16, 1966 and Luckey et al. U.S. Pat. 3,397,987 issued Aug. 20, 1968; the polyvalent metal salts described in Jones U.S. Pat. 2,839,405 issued June 17, 1958; the thiuronium salts described in Herz et al. U.S. Pat. 3,220,839 issued Nov. 30, 1965; the palladium, platinum and gold salts described in Trivelli et al. U.S. Pat. 2,566,263 issued Aug. 28, 1951 and Yutzy et al. U.S. Pat. 2,597,915 issued May 27, 1952.

In addition to the above-identified compounds, still other selenium-containing compounds are unexpectedly effective as emulsion stabilizers and antifoggants.

Included among these various compounds are sodium diphenyl-phosphinobenzene sulfonate selenide; potassium 2 - selenylbenzothiazole; 7-selenyl-1,3,4,6-tetraazaindene; 4 selenyl - 6 - methyl-1,3,3a,7-tetraazaindene; 1-ethylnaphtho-[1,2-d] selenazoline-2-thione and the like.

Various novel processes are employed in the preparation of some of these aforedescribed compounds.

In preparing guanidinium-2-selenylpropane sulfonate, 17 g. (0.07 mole) of 2-(3-sulfopropyl) - 2 - selenopseudourea and 10 ml. of ammonium hydroxide are heated gently on a steam bath, twirled slowly until the solid is all dissolved, then heated at 65° to 70° C. After removing from the steam bath, it is permitted to stand at room temperature for 3 hours. The resulting crystals are concentrated in vacuo to dryness and yields 16 g. Upon recrystallization from isopropyl alcohol and chloroform (1:1) a yield of 1 g. is obtained having a M.P. of 160° C.

The required 2-(3-sulfopropyl)-2-selenopseudo-urea is prepared from 39 g. (0.25 mole) of 1-bromo-3-chloropropane and 25 g. (0.20 mole) of sodium sulfite which are stirred and refluxed for 2 hours in 300 ml. of a 1:1 mixture of ethyl alcohol and water. This mixture is concentrated to about 100 ml. and 20 g. (0.17 mole) of selenourea is added. This mixture is stirred and refluxed for 1/2 hour, concentrated to 75 ml., then chilled. From a mushy, off-white cream, the final product is recrystallized from about 50 ml. of water in a 16 g. yield which has a melting point of 225° to 227° C.

Selenourea (6.3 g.; 0.05 mole) and 3,4-butanesultone (6.8 g.; 0.05 mole) are refluxed 24 hours in 50 ml. of acetonitrile. The resulting cake is recrystallized from water and then ethanol to give 2(1-methyl-3-sulfopropyl)-2-selenopseudo urea (3 g.; 0.03 mole) having a melting point of 260° C. This product is added to 7 ml. of 28 percent ammonium hydroxide and the mixture is heated gently until all of the 2(1-methyl-3-sulfopropyl)-2-selenopseudo urea has dissolved. The solution is heated to 80° C., allowed to stand at room temperature for 3 hours, and concentrated in vacuo to dryness. The resultant product is recrystallized from 50 ml. of ethyl alcohol, treated with decolorizing carbon, filtered and dried. There is thus obtained 4 g. of pale yellow crystals having a melting point of 185° C. These crystals are recrystallized from ethyl alcohol to yield 1 g. of guanidinium-3-selenyl-3-methylpropane sulfonate having the formula $$H—Se—CH(CH_3)—CH_2CH_2SO_3^{\ominus}(NH_2)_2C{=}NH_2^{\oplus}$$

This product has a melting point of 235° C.

Analysis.—Calcd. (percent): C, 21.8; H, 5.5; Se, 28.5.

Found (percent): C, 22.1; H, 5.2; Se, 28.2.

The potassium salt of 2-selenylbenzothiazole is prepared by the novel process of keeping in a nitrogen atmosphere 27.6 g. (0.2 mole) of potassium carbonate, 8.5 g. (0.05 mole) of 2-chlorobenzothiazole and 6 g. (0.05 mole) of selenourea during reflux. This is stirred overnight and hot filtered, then concentrated to dryness. The resulting solid is recrystallized from ethyl alcohol and treated with decolorizing carbon to yield 6 g. of substance having a melting point of greater than 280° C.

In combination with the various selenium- and sulfur-containing silver halide antifoggants and stabilizers, various polyazaindenes can be used with good results. For example, tri- and tetraazaindenes such as 1,3,4 and 1,3,5-tri and 1,2,3,4- and 1,2,3,5-tetraazaindenes are effective antifoggants when incorporated in the silver halide layer, a layer adjacent thereto and in various solutions, such as processing solutions and the like, used to contact the silver halide and other layers. These polyazaindenes are conveniently prepared from their corresponding diaminopyridines by conventional methods. An effective concentration range is from about 0.95 g. to about 4.0 g./mole of silver and preferably from about 0.75 g./mole to about 3.0 g./mole.

Based upon their incorporation into various processing solutions such as a hydroquinone type developer these polyazaindenes are effective in concentrations of from about 0.15 to about 0.75 gram/liter and preferably 0.25 to about 0.50 gram/liter of solution.

The silver halide emulsions used with this invention can comprise silver chloride, silver bromide, silver bromoiodide, silver chlorobromoiodide or mixtures thereof. The emulsions can be coarse or fine grain and can be prepared by any of the well-known procedures, e.g. single jet emulsions, double jet emulsions, such as Lippmann emulsions, ammoniacal emulsions, thiocyanate or thioether ripened emulsions such as those described in Nietz et al. U.S. Pat. 2,222,264 issued Nov. 19, 1940; Illingsworth U.S. Pat. 3,320,069 issued May 16, 1967; and McBride U.S. Pat. 3,271,157 issued Sept. 6, 1966. Surface image emulsions can be used or internal image emulsions such as those described in Davey et al. U.S. Pat. 2,592,250 issued May 8, 1952; Porter et al. U.S. Pat. 3,206,313 issued Sept. 14, 1965; Berriman U.S. Pat. 3,367,778 issued Feb. 6, 1968; and Bacon et al. U.S. Pat. 3,447,927 issued June 3, 1969. If desired, mixtures of surface and internal image emulsions can be used as described in Luckey et al. U.S. Pat. 2,996,382 issued Aug. 15, 1961. Negative type emulsions can be used or direct positive emulsions such as those described in Leermakers U.S. Pat. 2,184,013 issued Dec. 19, 1939; Kendall et al. U.S. Pat. 2,541,472 issued Feb. 13, 1951; Berriman U.S. Pat. 3,367,778 issued Feb. 6, 1968; Schouwenaars British Pat. 723,019 issued Feb. 2, 1955; Illingsworth et al. French Pat. 1,520,821 issued Mar. 4, 1968; Ives U.S. Pat. 2,563,785 issued Aug. 7, 1951; Knott et al. U.S. Pat. 2,456,953 issued Dec. 21, 1948, and Land U.S. Pat. 2,861,885 issued Nov. 25, 1958. The emulsions can be regular grain emulsions such as the type described in Klein and Moisar, J. Phot. Sci., vol. 12, No. 5, September/October 1964, pp. 242–251.

The emulsions used with this invention can be sensitized with chemical sensitizers, such as with reducing agents; sulfur, selenium or tellurium compounds; gold platinum or palladium compounds; or combinations of these. Suitable procedures are described in Sheppard et al. U.S. Pat. 1,623,499 issued Apr. 5, 1927; Waller et al. U.S. Pat. 2,399,083 issued Apr. 23, 1946; McVeigh U.S. Pat. 3,297,447 issued Jan. 10, 1967; and Dunn U.S. Pat. 3,297,446 issued Jan. 10, 1967.

The photographic and other hardenable layers used in the practice of this invention can be hardened by various organic or inorganic hardeners, alone or in combination, such as the aldehydes, and blocked aldehydes, ketones, carboxylic and carbonic acid derivatives, sulfonate esters, sulfonyl halides and vinyl sulfonyl ethers, active halogen compounds, epoxy compounds, aziridines, active olefins, isocyanates, carbodiimides, mixed function hardeners and polymeric hardeners such as oxidized polysaccharides like dialdehyde starch and oxyguar gum and the like.

The photographic emulsions and elements described in the practice of this invention can contain various colloids alone or in combination as vehicles, binding agents and various layers. Suitable hydrophilic materials include both naturally-occurring substances such as proteins, for example, gelatin, gelatin derivatives, cellulose derivatives, polysaccharides such as dextran, gum arabic and the like; and synthetic polymeric substances such as water soluble polyvinyl compounds like poly(vinylpyrrolidone), acrylamide polymers and the like.

The described photographic emulsion layers and other layers of a photographic element employed in the practice of this invention can also contain alone or in combination with hydrophilic, water permeable colloids, other synthetic polymeric compounds such as dispersed vinyl compounds such as in latex form and particularly those which increase the dimensional stability of the photographic materials. Suitable synthetic polymers include those described, for example, in Nottorf U.S. Pat. 3,142,568 issued July 28, 1964; White U.S. Pat. 3,193,386 issued July 6, 1965; Houck et al. U.S. Pat. 3,062,674 issued Nov. 6, 1962; Houck et al. U.S. Pat. 3,220,844 issued Nov. 30, 1965; Ream et al. U.S. Pat. 3,287,289 issued Nov. 22, 1966; and Dykstra U.S. Pat. 3,411,911 issued Nov. 19, 1968; particularly effective are those water-insoluble polymers of alkyl acrylates and methacrylates, acrylic acid, sulfoalkyl acrylates or methacrylates, those which have crosslinking sites which facilitate hardening or curing, those having recurring sulfobetaine units as described in Dykstra Canadian Pat. 774,054.

The photographic layers and other layers of a photographic element employed and described herein can be coated on a wide variety of supports. Typical supports include cellulose nitrate film, cellulose ester film, poly(vinyl acetal) film, polystyrene film, poly(ethylene terephthalate) film, polycarbonate film and related films or resinous materials, as well as glass, paper, metal and the like. Typically, a flexible support is employed, especially a paper support, which can be partially acetylated or coated with baryta and/or an alpha-olefin polymer, particularly a polymer of an alpha-olefin containing 2 to 10 carbon atoms such as polyethylene, polypropylene, ethylenebutane copolymers and the like.

The photographic layers employed in the practice of this invention can contain plasticizers and lubricants such as polyalcohols, e.g. glycerin and diols of the type described in Milton et al., U.S. Patent 2,960,404 issued Nov. 1, 1966; fatty acids or esters such as those described in Robijns U.S. Patent 2,588,765 issued Apr. 11, 1952, and Duane U.S. Patent 3,121,060 issued Feb. 11, 1964; and silicone resins such as those described in Du Pont British Patent 955,061 issued Apr. 15, 1964.

The compounds obtained in accordance with this invention can be used in a pod such as described in Land U.S. Patent 2,543,181 issued Feb. 27, 1951 or employed in the photographic element for diffusion transfer processes which utilize the undeveloped silver halide in nonimage areas of the negative to form a positive by dissolving the undeveloped silver halide and precipitating it on a silver layer in close proximity to the original silver halide emulsion layer. The compounds can also be used in diffusion transfer of an imagewise distribution of developer, coupler, or dye, from a light-sensitive layer to a second layer, while the two layers are in close proximity to one another. The compounds of particular interest for diffusion transfer processes are the compounds of general Formula I since these compounds contain the solubilizers sulfonic acid substituents.

The following examples are intended for a further understanding and description of our invention:

Example I

In order to demonstrate the unexpected fog reduction and emulsion stabilization imparted by various organic selenium derivatives and their sulfur analogs, to a gold and sulfur sensitized silver bromoiodide gelatin emulsion containing a carbocyanine spectral sensitizer, the emulsion is first adjusted to approximately pBr 3 and a pH of 6.3. This emulsion is then coated on a film support at about 0.46 g. of silver and 0.84 g.

gelatin per square foot. After the emulsion is dried down and exposed, the film is developed for 5 minutes in a hydroquinone methylated p-aminophenol developer at 20° C. with the following results wherein speed is expressed relatively as a reciprocal of exposure on an Eastman 1B sensitometer and is measured at a 0.3 density units above fog. A portion of this emulsion serves as a control and to other portions of the same emulsion are added the various selenium derivatives and their sulfur analogs, in order to demonstrate their unexpected antifogging activity.

TABLE I

| Compound in g./mole Ag | Fresh Rel. speed | Fresh Fog | Incubation at 2 week storage at 50% relative humidity, 48°C., fog |
|---|---|---|---|
| Control | 100 | .11 | .72 |
| 3 methyl-2-methylbenzo-thiazolium $ClO_4$ (.027) | 87 | .10 | .66 |
| 3-methyl-2-methylenebozo-selenazoline (.030) | 89 | .12 | .45 |

Example II

Samples of the same silver halide emulsion as that of Example I are employed except that these samples also contain a polyethylene oxide and quaternary pyridinium development accelerator. Processing is accomplished in a methylated p-aminophenol hydroquinone developer.

It can be seen that in contrast to the quaternary azolium salt the methylene bases of Formula III are unexpectedly more effective.

TABLE II

| Compound in g./mole Ag | Development in Elon-hydroquinone for 12 minutes at 20°C. Relative speed | Fog |
|---|---|---|
| Control | 100 | .64 |
| 3-methyl-2-methylbenzoxazolium $ClO_4$ (.021) | 102 | .64 |
| 3-methyl-2-methylenebenzoselenazoline (.030) | 102 | .43 |

Example III

Employing a similar emulsion as in Example I, the selenium-containing compounds of Formula I exhibit superior antifoggant activity, moreover the compounds stabilize the sensitivity of the emulsion.

TABLE III

| Compound in g./mole Ag | Original Speed | Original Fog | 2 wk. storage at 50% RH, 180°F. Speed | 2 wk. storage at 50% RH, 180°F. Fog | 12'Elon-hx. Speed | 12'Elon-hx. Fog |
|---|---|---|---|---|---|---|
| Control | 100 | .16 | 55 | .53 | 100 | .22 |
| Guanidinium-2-selenylpropanesulfonate (0.18 g.) | 95 | .09 | 78 | .14 | 100 | .14 |
| Guanidinium-2-selenylpropanesulfonate (0.27 g.) | 95 | .09 | 73 | .14 | 100 | .14 |

Example IIIA

A gold and sulfur sensitized silver bromoiodide emulsion is coated on a film support at about 350 mg. silver per ft.$^2$. The emulsion is exposed and developed for 4 minutes in a high contrast hydroqiunone developer at 20° C. This emulsion serves as the control and to portions of the same emulsion are added, in concentrations show hereafter, various selenium and sulfur compounds which correspond to Formula II, in order to demonstrate their unexpected antifogging activity when compared to compounds described in U.S. Patent 2,131,038.

TABLE

| Compound in millimoles/mole AgX | Fresh test Rel. speed | Fresh test Fog | 2 wk., inc. fog |
|---|---|---|---|
| Control | 100 | .08 | .34 |
| 3-ethyl-2,4-dimethylthiazolium pts (0.4) | 94 | .08 | .28 |
| 2(N-ethylacetamido)propene-1-thiol (0.4) | 100 | .07 | .19 |

TABLE

| Compound in millimoles/mole AgX | Fresh test Rel. speed | Fresh test Fog | 1 wk. inc. fog |
|---|---|---|---|
| Control | 100 | .16 | .15 |
| 2-ethyl-3,4-dimethylselenazolium pts (0.1) | 115 | .11 | .26 |
| 2(N-methylpropionamido)propene-1-selenol (0.1) | 110 | .12 | .10 |

It can be seen that compounds 2(N-ethylacetamido)-propane-1-thiol and 2(N-methylpropionamido)propane-1-selenol, which correspond to Formula II, are superior antifoggants over seemingly related compounds 3-ethyl-2,4 - dimethylthiazolium pts and 2-ethyl-3,4-dimethylselenazolium pts which are known antifoggants as described in U.S. Patent 2,131,038.

Example IV

A bromoiodide emulsion is prepared, coated and processsed as previously described in Example III. To portions of the emulsion are added the various compounds as described in the following table at the indicated concentrations. The results are as follows:

TABLE IV

| Compound in millimoles mole AgX | Fresh Rel. speed | Fresh Fog | 2 wk. inc. Rel. speed | 2 wk. inc. Fog | 4 wk. inc. fog |
|---|---|---|---|---|---|
| Control | 100 | .09 | 170 | .17 | .61 |
| o-(N-ethylacetamido)thiophenol (0.15) | 94 | .09 | 170 | .11 | .45 |
| o-(N-ethylacetamido)thiophenol (0.3) | 85 | .09 | 148 | .08 | .18 |
| o-(N-ethylacetamido)selenaphenol (0.15) | 100 | .10 | 141 | .09 | .22 |
| o-(N-ethylacetamido)selenaphenol (0.3) | 89 | .10 | 110 | .10 | .13 |

Example V

Using the same emulsion and coating system as in Example I, then processing in a high contrast-hydroquinone developer for 12 minutes at 68° F. produced the following results to show that exceptionally good results are obtained with a representative compound of this invention's Formula I. Even when combined with a known development accelerator which usually increases the fog level even in the presence of other antifoggants, the present compounds provide good antifogging results.

TABLE V

| | Compound in g./mole Ag | 12'methylated p-aminophenol-hydroquinone Speed | Fog |
|---|---|---|---|
| No. 1 | Control | 100 | .22 |
| No. 2 | No. 1 containing a quaternary pyridinium development accelerator. | 155 | .59 |
| No. 3 | No. 2 with 3 g. Na salt of 4-hydroxy-6-methyl-1,3,3a,7-tetraazaindene. | 174 | .57 |
| No. 4 | No. 2 with 0.06 g. guanidinium-3-selenyl-3-methylpropanesulfonate. | 159 | .35 |

The invention has been described in detail with particular reference to certain preferred embodiments thereof, but it will be understood that variations and modifications can be effected within the spirit and scope of the invention.

There is claimed:

1. A photographic element comprising a support bearing a light sensitive silver halide-containing layer and, in a concentration of from about 0.005 gram to about 50 grams per mole of silver, an organic compound having the structural formula:

(I)

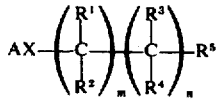

(II)

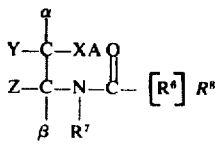

or (III)

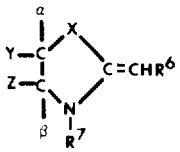

in which A is a cation selected from the group consisting of hydrogen, sodium, potassium, guanidinium, tetraalkylammonium, and trialkylsulfonium; X is sulfur or selenium; $R^1$ to $R^5$ are each hydrogen, an alkyl group having 1 to 6 carbon atoms or a substituted alkyl selected from the group consisting of haloalkyl, hydroxyalkyl and aryl alkyl, provided that at least one of said $R^1$ to $R^5$ is a sulfonic acid group or salt thereof; $R^6$ is hydrogen, an alkyl residue having 1 to 6 carbon atoms, an aryl residue or a halo-, hydroxy-, or aryl-substituted alkyl residue; $R^7$ is an alkyl residue having 1 to 6 carbon atoms, an aryl residue or a halo-, hydroxy-, or aryl-substituted alkyl residue; $\alpha$ and $\beta$ are each hydrogen, an alkyl residue having 1 to 6 carbon atoms, an aryl residue, a halo-, hydroxy-, or aryl-substituted alkyl residue or the electrons required to form double bonds between the carbon atoms: *$R^8$ is an alkyl residue having 1 to 6 carbon atoms, an aryl residue or a halo-, hydroxy-, or aryl-substituted alkyl residue;* Y and Z are each hydrogen, an alkyl residue having 1 to 6 carbon atoms, an aryl residue, a halo-, hydroxy-, or aryl-substituted alkyl residue or together provide the linkage required for completion of a cyclic nucleus selected from the group consisting of phenyl, naphthyl and pyridyl; and m and n are each 0 to 4 and the sum of m and n equals a positive integer up to 8.

2. A photographic element comprising a support bearing a light sensitive silver halide-containing layer and, in a concentration of from about 0.005 to about 1.0 gram per mole of silver, an organic compound having the structural formula:

(I)

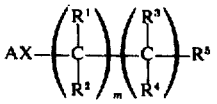

(II)

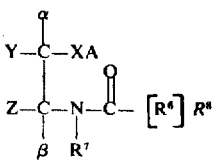

or (III)

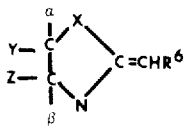

in which A is a cation selected from the group consisting of hydrogen, sodium, potassium, guanidinium, tetraalkylammonium, and trialkylsulfonium; X is sulfur or selenium; $R^1$ to $R^5$ are each hydrogen, an alkyl group having 1 to 6 carbon atoms or a substituted alkyl selected from the group consisting of haloalkyl, hydroxyalkyl and aryl alkyl, provided that at least one of said $R^1$ to $R^5$ is a sulfonic acid group or salt thereof; $R^6$ is hydrogen, an alkyl residue having 1 to 6 carbon atoms, an aryl residue or a halo-, hydroxy-, or aryl-substituted alkyl residue; $R^7$ is an alkyl residue having 1 to 6 carbon atoms, an aryl residue or a halo-, hydroxy-, or aryl-substituted alkyl residue; $\alpha$ and $\beta$ are each hydrogen, an alkyl residue having 1 to 6 carbon atoms, an aryl residue, a halo-, hydroxy-, or aryl-substituted alkyl residue or the electrons required to form double bonds between the carbon atoms; *$R^8$ is an alkyl residue having 1 to 6 carbon atoms, an aryl residue or a halo-, hydroxy-, or aryl-substituted alkyl residue;* Y and Z are each hydrogen, an alkyl residue having 1 to 6 carbon atoms, an aryl residue, a halo-, hydroxy-, or aryl-substituted alkyl residue or together provide the linkage required for completion of a cyclic nucleus selected from the group consisting of phenyl, naphthyl and pyridyl; and m and n are each 0 to 4 and the sum of m and n equals a positive integer up to 8.

3. The photographic element of claim 2 wherein at least one light sensitive silver halide-containing layer further comprises a phenolic, pyrazolone or open-chain reactive methylene coupler compound capable of forming a dye with an oxidation product of an aromatic primary amine silver halide color developing agent.

4. The photographic element of claim 2 whererin at least one light sensitive silver halide-containing layer further comprises a development modifier.

5. The element of claim 2 in which said compound is present in the silver halide-containing layer.

6. The element of claim 2 comprising the compound of Formula I corresponding to guanidinium-2-mercaptoethane sulfonate or guanidinium-2-selenylpropane sulfonate.

7. The element of claim 2 comprising the compound of Formula II corresponding to o-(N-ethylacetamido)-selenaphenol, 2(N-ethylacetamido)propene - 1 - thiol or 2(N-methylpropionamido)propene-1-selenol.

8. A photographic element comprising a support bearing a light sensitive silver halide-containing layer and, in a concentration of from about 1.0 gram to about 50 grams per mole of silver, an organic compound having the structural formula:

(I)

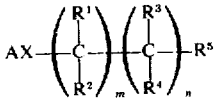

(II)

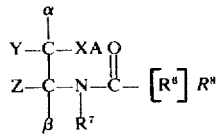

or (III)

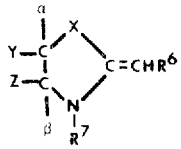

in which A is a cation selected from the group consisting of hydrogen, sodium, potassium, guanidinium, tetraalkylammonium, and trialkylsulfonium; X is sulfur or selenium; $R^1$ to $R^5$ are each hydrogen, an alkyl group having 1 to 6 carbon atoms or a substituted alkyl selected from the group consisting of haloalkyl, hydroxyalkyl and aryl alkyl, provided that at least one of said $R^1$ to $R^5$ is a sulfonic acid group or salt thereof; $R^6$ is hydrogen, an alkyl residue having 1 to 6 carbon atoms, an aryl residue or a halo-, hydroxy-, or aryl-substituted alkyl residue; $R^7$ is an alkyl residue having 1 to 6 carbon atoms, an aryl residue or a halo-, hydroxy-, or aryl-substituted alkyl residue; $\alpha$ and $\beta$ are each hydrogen, an alkyl residue having 1 to 6 carbon atoms, an aryl residue, a halo-, hydroxy-, or aryl-substituted alkyl residue or the electrons required to form double bonds between the carbon atoms: *$R^8$ is an alkyl residue having 1 to 6 carbon atoms, an aryl residue or a halo-, hydroxy-, or aryl-substituted alkyl residue;* Y and Z are each hydrogen, an alkyl residue having 1 to 6 carbon atoms, an aryl residue, a halo-, hydroxy-, or aryl-substituted alkyl residue or together provide the linkage required for completion of a cyclic nucleus selected from the group consisting of phenyl, naphthyl and pyridyl; and m and n are each 0 to 4 and the sum of m and n equals a positive integer up to 8.

9. The element of claim 8 in which said silver halide containing layer is an emulsion layer comprising gelatin as a binder.

*10. A photographic element comprising a support bearing a light sensitive silver halide-containing layer and, in a concentration of from about 0.005 gram to about 50 grams per mole of silver, an organic compound having the structural formula:*

(I)

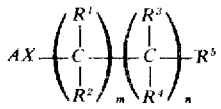

*in which A is a cation selected from the group consisting of hydrogen, sodium, potassium, guanidinium, tetraalkylammonium, and trialkylsulfonium; X is sulfur or selenium; $R^1$ to $R^5$ are each hydrogen, an alkyl group having 1 to 6 carbon atoms or a substituted alkyl selected from the group consisting of haloalkyl, hydroxyalkyl and aryl alkyl, provided that at least one of said $R^1$ to $R^5$ is a sulfonic acid group or salt thereof; and m and n are each 0 to 4 and the sum of m and n equals a positive integer up to 8.*

*11. A photographic element comprising a support bearing a light sensitive silver halide-containing layer and, in a concentration of from about 0.005 gram to about 50*

*grams per mole of silver, an organic compound having the structural formula:*

(II)

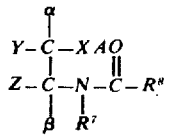

*in which A is a cation selected from the group consisting of hydrogen, sodium, potassium, guanidinium, tetraalkylammonium, and trialkylsulfonium; X is sulfur or selenium; $R^7$ is an alkyl residue having 1 to 6 carbon atoms, an aryl residue or a halo-, hydroxy-, or aryl-substituted alkyl residue; α and β are each hydrogen, an alkyl residue having 1 to 6 carbon atoms, an aryl residue, a halo-, hydroxy-, or aryl-substituted alkyl residue or the electrons required to form double bonds between the carbon atoms; $R^8$ is an alkyl residue having 1 to 6 carbon atoms, an aryl residue or a halo-, hydroxy-, or aryl-substituted alkyl residue; and Y and Z are each hydrogen, an alkyl residue having 1 to 6 carbon atoms, an aryl residue, a halo-, hydroxy-, or aryl-substituted alkyl residue or together provide the linkage required for completion of a cyclic nucleus selected from the group consisting of phenyl, naphthyl and pyridyl.*

*12. A photographic element comprising a support bearing a light sensitive silver halide-containing layer and, in a concentration of from about 0.005 gram to about 50 grams per mole of silver, an organic compound having the structural formula:*

(III)

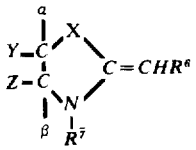

*in which X is sulfur or selenium; $R^6$ is hydrogen, an alkyl residue having 1 to 6 carbon atoms, an aryl residue or a halo-, hydroxy-, or aryl-substituted alkyl residue; $R^7$ is an alkyl residue having 1 to 6 carbon atoms, an aryl residue or a halo-, hydroxy-, or aryl-substituted alkyl residue; α and β are each hydrogen, an alkyl residue having 1 to 6 carbon atoms, an aryl residue, a halo-, hydroxy-, or aryl-substituted alkyl residue or the electrons required to form double bonds between the carbon atoms; Y and Z are each hydrogen, an alkyl residue having 1 to 6 carbon atoms, an aryl residue, a halo-, hydroxy-, or aryl-substituted alkyl residue or together provide the linkage required for completion of a cyclic nucleus selected from the group consisting of phenyl, naphthyl and pyridyl.*

* * * * *

UNITED STATES PATENT AND TRADEMARK OFFICE

CERTIFICATE OF CORRECTION

PATENT NO. : Re. 28,668

DATED : December 30, 1975

INVENTOR(S) : Arthur H. Herz and Edwin R. Westcott

It is certified that error appears in the above-identified patent and that said Letters Patent are hereby corrected as shown below:

Title page, 2nd column, 3rd formula, that part of the formula reading "$C=CHR^1$" should read ---$C=CHR^6$---.

Column 4, lines 54-55, "thiophenol;] o-(N-phenylformamido)thiophenol;" should read ---thiophenol; o-(N-phenylformamido)thiophenol;]---.

Column 5, line 6, "insurea" should read ---insure a---.

Column 7, line 34, "descrbied" should read ---described---.

Column 11, line 40, "-methylenebozo-" should read --- -methylenebenzo- ---.

Column 12, line 40, "show hereafter" should read ---shown hereafter---.

Column 13, first heading of Table IV, "millimoles mole AgX" should read --- millimoles/mole AgX ---.

Signed and Sealed this

Twenty-sixth Day of October 1976

[SEAL]

*Attest:*

RUTH C. MASON
*Attesting Officer*

C. MARSHALL DANN
*Commissioner of Patents and Trademarks*